United States Patent [19]

Sugawara et al.

[11] Patent Number: 5,026,876

[45] Date of Patent: Jun. 25, 1991

[54] PROCESS FOR PRODUCING MALEIC ANHYDRIDE

[75] Inventors: Harusige Sugawara; Takasi Okawa, both of Osaka, Japan

[73] Assignee: Mitsui Toatsu Chemicals, Inc., Tokyo, Japan

[21] Appl. No.: 467,377

[22] Filed: Jan. 19, 1990

[30] Foreign Application Priority Data

Jan. 25, 1989 [JP] Japan ................................. 1-13985
Apr. 7, 1989 [JP] Japan ................................. 1-87014

[51] Int. Cl.$^5$ ........................................... C07D 307/60
[52] U.S. Cl. ................................. 549/257; 549/203; 549/258; 549/259; 549/262
[58] Field of Search ............... 549/203, 262, 257, 258, 549/259

[56] References Cited

FOREIGN PATENT DOCUMENTS 41-19405 11/1966 Japan .
49-110624 10/1974 Japan .
49-116023 11/1974 Japan .

*Primary Examiner*—Bernard I. Dentz
*Attorney, Agent, or Firm*—Burns, Doane, Swecker & Mathis

[57] ABSTRACT

Crude maleic anhydride produced by catalytic oxidation is distilled and then n-propyl gallate, cuprous chloride and zinc chloride are added thereto.

Alternatively, crude maleic anhydride is distilled in the presence of tridecyl phosphite. Further, these procedures can be used in combination. Thermal stability and color stability of the maleic anhydride is improved.

6 Claims, No Drawings

PROCESS FOR PRODUCING MALEIC ANHYDRIDE

BACKGROUND OF THE INVENTION (1) Field of the Invention

The present invention relates to a process for producing maleic anhydride, and more particularly, to a process for producing maleic anhydride of improved thermal stability and color stability.

(2) Description of the Related Art

Maleic anhydride is an unsaturated dibasic acid obtainable by the catalytic oxidation of benzene or a fraction of hydrocarbons containing 4 carbon atoms (hereinafter referred to as the $C_4$ fraction). Maleic anhydride has two carboxyl groups in the form of acid anhydride and a highly reactive double bond so that maleic anhydride is used for various reactions.

Maleic anhydride is highly useful and has been widely used as a raw material for producing synthetic rubbers, plasticizers, synthetic resins, adhesive agents, synthetic fibers, synthetic leathers, agricultural chemicals, and the like.

Maleic anhydride is usually produced by catalytically oxidizing benzene or the $C_4$ fraction in a vapor phase and distilling the resulting reaction products. However, maleic anhydride obtained by distillation still contains trace amounts of impurities that are difficult to separate such as by-products produced during the oxidation. Therefore, the thus-obtained maleic anhydride lacks thermal stability and has a tendency to become discolored when heat-melted. In particular, this tendency becomes marked when maleic anhydride is stored for a long period of time. This discoloring upon heat-melting exerts adverse effects on the quality of secondary products produced from maleic anhydride and impairs their commercial value to a great extent.

Accordingly, it is strictly required that maleic anhydride for industrial use be free from the discoloration phenomenon upon heating and melting, and during storing for a long time.

In view of the above, various methods have been proposed for the prevention of the discoloration of maleic anhydride.

For example, in Japanese Patent Publication No. 19,405/66 is disclosed a method for improving the thermal stability of maleic anhydride, in which a compound represented by the following general formula:

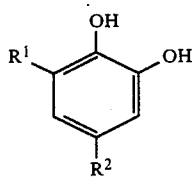

(wherein $R^1$ represents -H or -OH; and $R^2$ represents -H, -C(CH_3)_3, -COOH or an aliphatic ester thereof) is added to maleic anhydride, optionally together with zinc, copper, aluminum or an oxide or salt thereof such as cuprous chloride, zinc chloride, aluminum chloride and the like. In the method described in Japanese Patent Publication No. 26,766/72, hydroquinone is added to maleic anhydride in combination with elemental copper, molybdenum a copper or molybdenum compound, or a mixture of these, in order to stabilize the color of molten maleic anhydride. In Japanese Patent Publication No. 51,393/82 is disclosed a method for stabilizing the color of maleic anhydride, which comprises incorporating an organic phosphoric polyester, a metal salt of fluoroboric acid, a metallic copper and a copper compound into purified maleic anhydride. In Japanese Patent Application (Laid Open) No. 116,023/74 is described a method in which a phosphorous ester or a mixture of a phosphorous ester and a metal halide is added to maleic anhydride, so as to improve the thermal stability thereof. In Japanese Patent Application (Laid-Open) No. 23,719/73, maleic anhydride is stabilized against discoloration at elevated temperatures through the addition of thiophosphoric hydrocarbinol.

However, none of these prior art methods is able to fully meet the severe requirements in quality of recent years.

OBJECTS AND SUMMARY OF THE INVENTION

It is an object of the present invention to provide a process for producing maleic anhydride having thermal stability and color stability by distillation of crude maleic anhydride.

It is another object of the present invention to provide a process for producing maleic anhydride exhibiting excellent thermal stability and color stability upon storing for a long period of time at a molten or solidified state, the maleic anhydride having been purified by distillation.

According to one aspect of the present invention, there is provided a process for producing maleic anhydride by the catalytic oxidation of benzene and/or a fraction of hydrocarbons containing 4 carbon atoms which comprises distilling crude maleic anhydride, and adding n-propyl gallate, cuprous chloride and zinc chloride to the thus-distilled maleic anhydride.

According to another aspect of the present invention, there is provided a process for producing maleic anhydride by the catalytic oxidation of benzene and/or a fraction of hydrocarbons containing 4 carbon atoms which comprises adding tridecyl phosphite to crude maleic anhydride and distilling the crude maleic anhydride.

According to a further aspect of the present invention, there is provided a process for producing maleic anhydride by the catalytic oxidation of benzene and/or a fraction of hydrocarbons containing 4 carbon atoms which comprises distilling crude maleic anhydride to which tridecyl phosphite has been added, and adding n-propyl gallate, cuprous chloride and zinc chloride to the thus-distilled maleic anhydride.

DESCRIPTION OF THE PREFERRED EMBODIMENTS

Starting materials for producing maleic anhydride are benzene or the $C_4$ fraction which may be produced by decomposing, for example, naphtha. The $C_4$ fraction is mainly composed of n butane (at least 96% by weight) and the other components are isobutane, propane, pentane and the like.

Upon catalytically oxidizing benzene or the $C_4$ fraction there is usually used a catalyst of a vanadium-molybdenum system or a vanadium-phosphorus system. The catalytic oxidation is usually affected at 350°–550 C.

Reaction products produced by catalytic oxidation of benzene or the $C_4$ fraction are cooled to 70°–90° C. to obtain crude maleic anhydride. A part of the resulting maleic anhydride absorbs water so as to be converted to maleic acid. By dehydrating the maleic acid, there is produced again crude maleic anhydride, which is then distilled in the presence of tridecyl phosphite as a phosphorus series antioxidant.

The method of adding tridecyl phosphite may be batchwise or continuous. From the standpoint of actual operation, a continuous addition is preferable. It is preferable that tridecyl phosphite is added to crude maleic anhydride in an amount to result in a given concentration before feeding the crude maleic acid to a distillation tower. The amount of tridecyl phosphite is preferably 50–500 ppm, more preferably 100–200 ppm based on crude maleic anhydride.

After adding tridecyl phosphite, the crude maleic anhydride may be distilled without thermal treatment, but the thermal treatment enhances further the stabilities. The thermal treatment can be carried out at a temperature range of from the melting point of crude maleic anhydride and boiling point thereof, preferably at 120°–190° C. The time required for the thermal treatment is 1–10 hours. The thermal treatment may be batchwise or continuously affected. Any procedure is usable as far as tridecyl phosphite can be uniformly dispersed and heated. Distillation of crude maleic anhydride gives purified maleic anhydride. Distillation can be affected at a pressure of 50–100 mm Hg at the bottom temperature of a distillation tower of 120°–160° C.

To the thus-distilled maleic anhydride are added stabilizers which are n-propyl gallate, cuprous chloride, and zinc chloride according to the present invention. The way of adding stabilizers is not particularly limited. For example, stabilizers are added to maleic anhydride distilled from a distillation step or stored at a molten state and properly mixed and stirred. N-propyl gallate and cuprous chloride may be separately added, or added in the form of a mixture previously prepared. The order of addition upon adding separately is not limited. Then, zinc chloride may be directly added as it is or zinc chloride dissolved in water, or an organic solvent such as ethanol and the like may be added. In any way of adding zinc chloride the desired effect can be obtained. The amounts of stabilizers added are preferably 1–100 ppm by weight of n-propyl gallate and 0.1–5 ppm by weight of cuprous chloride. Further, the amount of zinc chloride may be preferably selected from the range of 0.1 to 5 ppm by weight.

A color stabilizer composition where n-propyl gallate and cuprous chloride are used in combination has been already proposed in Japanese Patent Publication No. 19405/66, but does not meet the requirements of present days on the thermal stability upon heat-melting and the prevention of coloring of maleic anhydride. Surprisingly, the present inventors have found that markedly improved thermal stability can be attained by using zinc chloride in combination with the known combination of n-propyl gallate and cuprous chloride. As shown in Comparative Examples described hereinbelow, effects attainable by the combination of n-propyl gallate and cuprous chloride are far inferior to those attainable by the combination of the present invention even if the former two compounds are used in larger quantities. Results are also poor when zinc chloride alone is employed.

It is undesirable to incorporate large quantities of stabilizers into maleic anhydride since they act as impurities and can cause adverse effects on the quality of maleic anhydride, in particular, on the various chemical properties thereof. The combination of stabilizers according to the present invention exhibits satisfactory effects even when used in small quantities and, hence, causes no adverse effects on the quality of maleic anhydride. The combination of the stabilizers therefore exerts no adverse effects on secondary products produced from maleic anhydride stabilized by them.

According to the present invention, thermal stability and color stability of maleic anhydride obtained by distillation is remarkably improved only by adding tridecyl phosphite upon distillation.

Addition of a stabilizer to the maleic anhydride obtained by the distillation results in a further improvement in thermal stability and color stability. According to the present invention, zinc chloride is added to the conventional combination of n-propyl gallate and cuprous chloride, and the hue of a high temperature molten color of maleic anhydride can be lightened to a level which has not been heretofore attained.

Furthermore, deterioration of color with the lapse of time upon storing at a molten state can be suppressed to a great extent. In addition, only small amounts of the stabilizers are enough to give the desired effect and therefore, such stabilizers do not adversely affect at all as impurities, but markedly contribute to improvement in quality of maleic anhydride.

The process of the present invention will be explained further in detail below.

In the following examples, "ppm" is by weight. "Molten color" indicates the APHA of the hue of maleic anhydride measured in molten state in accordance with JIS (Japanese Industrial Standards K-1359, and "heat-melted color" indicates the APHA of the hue of maleic anhydride which has been placed in a quartz test tube having a diameter of ca. 20 mm and a height of 150 mm (the same test tube used in the determination of molten color according to JIS K-1359) and heat-melted by dipping the test tube for 60 minutes in an oil bath maintained at a temperature of 181° C.

EXAMPLE 1

Into a four-necked glass flask was charged 3,000g of crude maleic anhydride prepared by the catalytic oxidation (catalyst: divanadyl pyrophosphate, reaction temperature: 430° C.) of $C_4$ fraction (Composition: isobutane 0.8 wt%, n-butane 98.0 wt% and pentanes 1.2 wt%), and then tridecyl phosphite ("Mark 3010", tradename, manufactured by Adeca Argus Co.,Ltd.) gas added thereto up to a concentration of 200 ppm. The flask gas fitted into a packed rectification tower (Packing: Helipack S-2; size of packed portion: 30 mm in diameter X 1200 mm in height), and distillation was carried out under a pressure of 70 mm Hg at a reflux ratio of 3 while maintaining the still temperature at 125° C. by adjusting the pressure at the top of tower. Stabilizers were added to the purified maleic anhydride fraction at a distillation rate of 20 to 90%. As stabilizers, 5 ppm of n-propyl gallate and 1 ppm of cuprous chloride were added.

A sample of the maleic anhydride containing said stabilizers thus prepared was allowed to stand at a solid state for 24 hours and the other sample thereof under the same condition as above for 30 days. Then, both of them were remelted and the molten color and thermal stability (heat-melted color) were tested.

Further, maleic anhydride was obtained by distillation without adding tridecyl phosphite. 5 ppm of n-propyl gallate and 1 ppm of cuprous chloride as stabilizers were added. The maleic anhydride was tested with respect to molten color and thermal stability (heat-melted color). The results are shown in Table 1.

TABLE 1

|  | Molten Color (APHA) | Thermal Stability (APHA) | |
|---|---|---|---|
|  |  | After 24 hrs. | After 30 Days |
| Example 1 | <10 | 25 | 200 |
| Control | 10 | 300 | >500 |

Control: Tridecyl phosphite was not added.

EXAMPLES 2-3

The procedure of Example 1 was repeated except that the amount of tridecyl phosphite was changed. The thus-purified maleic anhydride was determined as to molten color and thermal stability (heat-melted color). The results are shown in Table 2.

TABLE 2

|  | Concentration of TDPH Added (ppm) | Molten Color (APHA) | Thermal Stability (APHA) | |
|---|---|---|---|---|
|  |  |  | After 24 hrs. | After 30 Days |
| Example 2 | 50 | <10 | 60 | 300 |
| Example 3 | 500 | <10 | 25 | 150 |

TDPH: Tridecyl Phosphite

EXAMPLES 4-7

The procedure of Example 1 was repeated except that thermal treatment was affected. The thus-purified maleic anhydride was determined with respect to molten color and thermal stability (heat-melted color). The results are shown in Table 3.

TABLE 3

|  | Thermal Treatment | | Molten Color (APHA) | Thermal Stability (APHA) | |
|---|---|---|---|---|---|
|  | °C. | hr |  | After 24 hrs. | After 30 Days |
| Example 4 | 135 | 4 | 10 | 50 | 120 |
| Example 5 | 150 | 4 | 10 | 35 | 100 |
| Example 6 | 185 | 4 | 10 | 20 | 80 |
| Example 7 | 185 | 8 | 10 | 20 | 80 |

COMPARATIVE EXAMPLES 1-3

The procedure of Example 1 was repeated except that 800 g of crude maleic anhydride prepared in the same way as in Example 1 was charged into a four-necked glass flask and sulfosalicylic acid, phophorous acid or a combination of zinc chloride and basic aluminum magnesium carbonate [$Mg_6Al_2(OH)_{16}CO_3 \cdot 4H_2O$, tradename, "Kyowaad 500" manufactured by Kyowa Kagaku Kogyo Co., Ltd.] was added and then thermal treatment was affected at 135° C. for 60 minutes. The thus-purified maleic anhydride was tested with respect to molten color and thermal stability (heat-melted color). The results are shown in Table 4.

TABLE 4

| Comparative Example | Treating Agent | Molten Color (APHA) | Thermal Stability (APHA) | |
|---|---|---|---|---|
|  |  |  | After 24 hrs. | After 30 Days |
| 1 | Sulfosalicylic acid (0.1% by weight) | 10 | 100 | >500 |
| 2 | Phosphorous acid (30 ppm) | 10 | 50 | >500 |
| 3 | Zinc chloride (1% by weight) + Kyowaad 500 (5% by weight) | 10 | 180 | >500 |

EXAMPLES 8-11

To crude maleic anhydride prepared following the procedure of Example 1 was added 200 pp of tridecyl phosphite followed by thermally treating at 180° C. for 4 hours and distilling in the same way as in Example 1. Particular amounts of n-propyl gallate, cuprous chloride and further zinc chloride were added to a molten maleic anhydride thus purified by distillation followed by uniformly stirring and mixing, and then the resulting mixture gas placed in a quartz test tube to measure the molten color and heat-melted color. The results are shown in Table 5.

COMPARATIVE EXAMPLE 4-8

Various stabilizers were combined and molten color and heat-melted color were measured in a way similar to Examples 8-11. The results are shown in Table 6.

EXAMPLE 12-17

Stabilizers were added in a way similar to Examples 8-11. In order to determine the change over time, samples to which various stabilizers were added were stored for 30 days at a liquid state (65° C.) and a solid state, and measured as to molten color and heat-melted color. The results are shown in Table 7.

TABLE 5

|  | Stabilizers | | Items Determined | |
|---|---|---|---|---|
|  | Kind | Amount Added (ppm) | Molten Color (APHA) | Heat-melted Color (APHA) |
| Reference Example 1 | not added | 0 | 5 | 250 |
| Example 8 | n-Propyl gallate | 5 | 5 | 10 |
|  | Cuprous chloride | 1 |  |  |
|  | zinc chloride | 0.5 |  |  |
| Example 9 | n-Propyl gallate | 5 | 5 | 5 |
|  | Cuprous chloride | 1 |  |  |
|  | zinc chloride | 1.0 |  |  |
| Example 10 | n-Propyl gallate | 5 | 5 | 5 |
|  | Cuprous chloride | 1 |  |  |
|  | zinc chloride | 2.0 |  |  |
| Example 11 | n-Propyl gallate | 5 | 5 | 5 |
|  | Cuprous chloride | 1 |  |  |
|  | zinc chloride | 5.0 |  |  |

TABLE 6

|  | Stabilizers | | Items Determined | |
|---|---|---|---|---|
|  | Kind | Amount Added (ppm) | Molten Color (APHA) | Heat-melted Color (APHA) |
| Reference Example 1 | not added | 0 | 5 | 250 |
| Comparative | n-Propyl gallate | 5 | 5 | 25 |

TABLE 6-continued

|  | Stabilizers |  | Items Determined |  |
|---|---|---|---|---|
|  | Kind | Amount Added (ppm) | Molten Color (APHA) | Heat-melted Color (APHA) |
| Example 4 | Cuprous chloride | 1 |  |  |
| Comparative Example 5 | Copper fluoroborate | 1 | 5 | 25 |
|  | Tri(2-chloroethyl) phosphate | 10 |  |  |
| Comparative Example 6 | Hydroquinone | 8 | 5 | 30 |
|  | Copper acetate (monohydrate) | 6 |  |  |
| Comparative Example 7 | Manganese chloride | 1 | 10 | 35 |
|  | Triphenylphosphite | 5 |  |  |
| Comparative Example 8 | n-Propyl gallate | 5 | 5 | 50 |
|  | zinc chloride | 1 |  |  |

TABLE 7

|  | Stabilizers |  | Items Determined |  |  |  |
|---|---|---|---|---|---|---|
|  |  |  | Molten Color (APHA) |  | Heat-melted Color (APHA) |  |
|  | Kind | Amount added (ppm) | Immediately After Addition | After 30 Days | Immediately After Addition | Stored in Liquid State | Stored in Solid State |
| Reference Example 2 | not added | 0 | 5 | 10 | 300 | >500 | >500 |
| Example 12 | n-Propyl gallate | 10 | 5 | 10 | 10 | 10 | 15 |
|  | Cuprous chloride | 1 |  |  |  |  |  |
|  | Zinc chloride | 0.5 |  |  |  |  |  |
| Example 13 | n-Propyl gallate | 5 | 5 | 5 | 10 | 10 | 10 |
|  | Cuprous chloride | 1 |  |  |  |  |  |
|  | Zinc chloride | 0.2 |  |  |  |  |  |
| Example 14 | n-Propyl gallate | 2 | 5 | 5 | 10 | 10 | 10 |
|  | Cuprous chloride | 1 |  |  |  |  |  |
|  | Zinc chloride | 0.2 |  |  |  |  |  |
| Example 15 | n-Propyl gallate | 2 | 5 | 5 | 15 | 15 | 20 |
|  | Cuprous chloride | 0.5 |  |  |  |  |  |
|  | Zinc chloride | 0.2 |  |  |  |  |  |
| Example 16 | n-Propyl gallate | 1 | 5 | 5 | 25 | 25 | 25 |
|  | Cuprous chloride | 0.25 |  |  |  |  |  |
|  | Zinc chloride | 0.2 |  |  |  |  |  |
| Example 17 | n-Propyl gallate | 1 | 5 | 5 | 30 | 30 | 35 |
|  | Cuprous chloride | 0.5 |  |  |  |  |  |
|  | Zinc chloride | 0.1 |  |  |  |  |  |

We claim:

1. In a process for producing maleic anhydride by the catalytic oxidation of benzene and /or a fraction of hydrocarbons containing 4 carbon atoms, the improvement which comprises adding tridecyl phosphite to crude maleic anhydride, and distilling the crude maleic anhydride.

2. In a process for producing maleic anhydride by the catalytic oxidation of benzene and/or a fraction of hydrocarbons containing 4 carbon atoms, the improvement which comprises
   (a) distilling crude maleic anhydride to which tridecyl phosphite has been added, and
   (b) adding n-propyl gallate, cuprous chloride and zinc chloride to the thus-distilled maleic anhydride.

3. The process according to claim 2 in which the bottom temperature of a distillation tower is kept at 120°–160° C.

4. The process according to claim 2 in which tridecyl phosphite is added to the crude maleic anhydride, the crude maleic anhydride being thermally treated and then distilled.

5. The process according to claim 4 in which the thermal treatment is affected at 120°–190° C.

6. The process according to claim 2 in which 1–100 ppm of n-propyl gallate, 0.1–5 ppm of cuprous chloride and 0.1–5 ppm of zinc chloride in terms of ppm by weight are added to the thus-distilled maleic anhydride.

* * * * *